United States Patent
Lyytikäinen et al.

(10) Patent No.: US 10,500,381 B2
(45) Date of Patent: Dec. 10, 2019

(54) DRUG DELIVERY SYSTEM

(71) Applicant: BAYER OY, Turku (FI)

(72) Inventors: Heikki Lyytikäinen, Naantali (FI); Harri Jukarainen, Kuusisto (DE)

(73) Assignee: BAYER OY, Turku (FI)

( * ) Notice: Subject to any disclaimer, the term of this patent is extended or adjusted under 35 U.S.C. 154(b) by 0 days.

(21) Appl. No.: 14/371,848

(22) PCT Filed: Jan. 22, 2013

(86) PCT No.: PCT/FI2013/050068
§ 371 (c)(1),
(2) Date: Jul. 11, 2014

(87) PCT Pub. No.: WO2013/110856
PCT Pub. Date: Aug. 1, 2013

(65) Prior Publication Data
US 2014/0350488 A1    Nov. 27, 2014

(30) Foreign Application Priority Data
Jan. 23, 2012  (FI) ..................................... 20125069

(51) Int. Cl.
*A61K 9/00* (2006.01)
*A61K 47/02* (2006.01)
*A61M 31/00* (2006.01)

(52) U.S. Cl.
CPC ......... *A61M 31/002* (2013.01); *A61K 9/0024* (2013.01); *A61K 9/0036* (2013.01); *A61K 9/0039* (2013.01); *A61K 9/0092* (2013.01); *A61K 47/02* (2013.01)

(58) Field of Classification Search
None
See application file for complete search history.

(56) References Cited

U.S. PATENT DOCUMENTS

| 5,660,848 A | 8/1997 | Moo-Young | |
|---|---|---|---|
| 5,916,595 A * | 6/1999 | Chen | A61K 9/0004 424/480 |
| 2002/0028788 A1* | 3/2002 | Bunt | A61K 9/0034 514/58 |
| 2005/0013863 A1* | 1/2005 | Lim | A61K 9/2853 424/472 |
| 2005/0203186 A1 | 9/2005 | Kraass | |
| 2005/0214251 A1 | 9/2005 | Pohl | |
| 2006/0024362 A1 | 2/2006 | Seth | |
| 2006/0165776 A1* | 7/2006 | Sesha | A61K 9/4808 424/451 |
| 2007/0148153 A1* | 6/2007 | Shlieout | A61K 9/1635 424/94.3 |
| 2007/0293837 A1 | 12/2007 | Sokal et al. | |
| 2009/0142313 A1 | 6/2009 | Talling et al. | |
| 2009/0208575 A1 | 8/2009 | Gunupati et al. | |
| 2010/0285097 A1 | 11/2010 | Talling et al. | |
| 2011/0208135 A1 | 8/2011 | Hakala | |

FOREIGN PATENT DOCUMENTS

| EP | 2140860 A1 | 1/2010 |
|---|---|---|
| JP | 2005-526739 A | 9/2005 |
| WO | 01/85132 A1 | 11/2001 |
| WO | 2002/032433 | 4/2002 |
| WO | 2003/017971 | 3/2003 |
| WO | 03/074034 A1 | 9/2003 |
| WO | 2006005794 A1 | 1/2006 |
| WO | 2006/085335 A2 | 8/2006 |
| WO | 2008/061963 | 5/2008 |
| WO | 2009/066006 A1 | 5/2009 |
| WO | 2010/000943 A1 | 1/2010 |
| WO | 2010/058070 A1 | 5/2010 |
| WO | WO2012092283 * | 7/2012 |

OTHER PUBLICATIONS

Cimbar, Talc MSDS, Apr. 2012.*
Science Lab, Silica MSDS, Oct. 2005.*
PCT International Search Report and Written Opinion for International Patent Application No. PCT/FI2013/050068, dated Jun. 11, 2013, 10 pages.
PCT International Preliminary Report on Patentability for International Patent Application No. PCT/FI2013/050068, dated Jul. 29, 2014, 7 pages.
Huang, et al., "On the importance and mechanisms of burst release in matrix-controlled drug delivery systems", Journal of Controlled Release, 73, (2-3), 2001, pp. 121-136.
Lee, "Effect of non-uniform initial drug concentration distribution on the kinetics of drug release from glassy hydrogel matrices", Polymer vol. 25, Issue 7, Jul. 1984, pp. 973-978.

* cited by examiner

*Primary Examiner* — Jennifer A Berrios
(74) *Attorney, Agent, or Firm* — McBee Moore Woodward & Vanik IP, LLC

(57) ABSTRACT

The present invention provides a novel drug delivery system for the controlled release of therapeutically active substances at a predetermined, essentially constant release rate over a prolonged period of time. The delivery system comprises at least one core comprising said therapeutically active substance(s), at least one membrane encasing the core and an intermediary layer of a substantially inert material, wherein the intermediary layer is applied between the core and the membrane or between two membrane layers.

12 Claims, 2 Drawing Sheets

DRUG DELIVERY SYSTEM

The present invention provides a novel drug delivery system for the controlled release of therapeutically active substances at a predetermined, essentially constant release rate over a prolonged period of time. The delivery system comprises at least one core comprising said therapeutically active substance(s), at least one membrane encasing the core and an intermediary layer of a substantially inert material, wherein the intermediary layer is applied between the core and the membrane or between two membrane layers.

BACKGROUND OF THE INVENTION

Several types of polymer based controlled release systems and a wide range of applications thereof have been presented in the literature. In most systems the mechanism controlling the release rate is based on diffusion, chemical reaction or solvent activation.

Diffusion controlled systems can typically be divided into reservoir, matrix and hybrid devices.

Reservoir drug delivery devices have a polymer membrane encasing the active agent. The active agent can be in the solid or in the liquid state, and the membrane can be microporous or non-porous. Upon activation, the active substance diffuses through the membrane at a controllable rate. As long as the drug core can be maintained in a saturated solid or suspension state, the release rate of the drug will be constant versus time until exhaustion of the active substance excess.

The saturated state would be difficult to maintain for drugs having low fluid solubility. Further, although the requirements for constant release would be met, the release will generally not be constant in the initial and end period. When the system is placed in a release medium, it takes a certain time for the system to reach a steady state and either a lag time or an initial burst is observed. If the membrane does not contain drug molecules at the time of placement, an induction period will be needed to saturate the membrane. Burst release is often observed in reservoir systems stored for some time prior to use. During storage the agent saturates the entire membrane. When placed in a release medium, the agent that has diffused to the surface of the membrane is released immediately, causing a burst effect. Also dose dumping due to minor flaws in the coating can lead to burst release even prior to patient administration.

Toward the end of the release period the concentration of the dissolved drug in the core will decrease below the saturation point and as a result the release rate will decrease.

In the matrix system the drug is dissolved or dispersed in a polymer matrix. The release rate is often proportional to the square root of elapsed time. The release behavior of these systems is dependent on the physical properties of the drug, drug load, particle size, solubility of the drug in the polymer and diffusivity in the polymer matrix. In addition, the shape of the device, surface area and the path length of diffusion are also important parameters. With these systems the release rate will decrease with time as a result of increasing path length for the drug solutes to diffuse from the center of the device to the surface. One proposed method to improve the consistency of release is to use systems with uneven initial drug distributions, with higher loading concentrations towards the center of the device (Lee, Polymer 25 (1984), pp. 973-978).

In a hybrid system, another type of matrix device, the active substance is homogeneously dispersed in the polymer matrix, which is covered by a rate limiting membrane. Drug release is controlled by both the polymer membrane and the matrix. Drug dissolves first into the core polymer, dissolved drug travels by diffusion towards the inner surface of the membrane, dissolves in the membrane, diffuses through the membrane to the outer surface of the membrane and dissociates finally into the surrounding media. The release rate can be accurately adjusted with this system, but initial burst can take place and toward the end of the release period the release rate commonly decreases.

Burst release may be the optimal mechanism of delivery in rare instances, but is often problematic because it is unpredictable and, even when the burst is desired, the amount of burst cannot be significantly controlled. The initial high release rates may lead to drug concentrations near or above the toxic level in vivo. Any drug released during the burst stage may also be metabolized and excreted without being effectively utilized. Even if no harm is done during the burst release, this amount of drug is essentially wasted, and the ineffective drug usage may have therapeutic and economic effects.

Methods to prevent or minimize the burst effect in a wide range of polymer/drug systems have been described and include for example surface extraction of the active agent prior to in vivo usage, using double-walled microspheres with layers made of different inert or erodible polymers, and modifying the surfaces of the drug-loaded matrix via an outer layer of polymer coating [see for example Xiao Huang and Christopher S Brazel Journal of Controlled Release, 73, (2-3), 2001, 121-136]. Unfortunately, many of the methods involve additional costly steps, which are not necessarily suitable for pharmaceuticals and in any case result in reduced drug loading percentages or the introduction of additional materials.

The traditional way to adjust the release rate of a drug substance in a polymer based delivery system has been to change different parameters, such as the area of the device, the thickness of the membrane; the drug load in the core, the core and membrane material, end capping the device or incorporating fillers into the polymer composition of the membrane. By increasing the loading of filler, steric hindrance or diffusion path increase to slow down the release of the active substance. For an ideal delivery system the predetermined release rate should also remain as constant as possible during the whole life-span of the device. This would be important to maintain the daily dosage of the drug in a therapeutically effective window long enough, and still lower the total amount of drug administered to the patient. It would also enable reasonably low drug load in the device so that the disposal of the device after the treatment period would be less problematic and would satisfy environmental requirements.

U.S. Pat. No. 5,660,848 discloses an implantable drug delivery device comprising a matrix core, an outer layer, and an intermediate layer between the core and the outer layer. The intermediate layer is made of porous polymeric material, preferably cellulose or regenerated cellulose. WO 03/017971 discloses an embodiment wherein a drug delivery system comprises a core and two elastomer membrane layers of different thickness for controlling the release rate of active agents. The elastomer membrane is preferably a siloxane-based elastomer, such as poly(dimethylsiloxane) (PDMS) or poly(ethylene oxide)-PDMS. In US 2005/0214251, drug formulations for sublingual and subcutaneous administration of insulin are disclosed. In one embodiment the formulation may be in the form of a film comprising a bottom layer and a top layer which surround a core layer containing the active agent.

OBJECT OF THE INVENTION

The object of the present invention is to provide a novel drug delivery system for the controlled release of at least one therapeutically active substance at a predetermined, essentially constant release rate over a prolonged period of time. The delivery system comprises at least one core comprising said therapeutically active substance(s), at least one membrane encasing the core and an intermediary layer of an inert material applied between the core and the membrane or between two membranes. The intermediary layer is capable of preventing direct contact between the core and the membrane or between two membrane layers but is not covalently bound to any of them. Preferably said intermediary layer comprises particulate matter, particles, granules, crystals, micro- or nanoscaled crystals or powder in a solid, suspended or gel form.

A further object of the invention is to provide a drug delivery system having no or only minimal initial burst.

BRIEF DESCRIPTION OF THE FIGURES

The invention is further illustrated by the following examples, describing various constructions of the drug delivery system according to the invention.

DETAILED DESCRIPTION OF THE INVENTION

Figure 1:
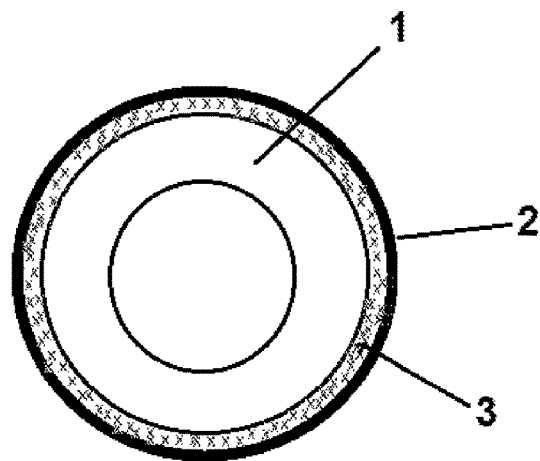
FIG. 1 is a schematic view of a delivery system comprising a core 1 comprising a therapeutically active agent, a membrane 2 and an intermediary layer 3 comprising inert particles and applied between the outer surface of the core 1 and the inner surface of a membrane layer.

The advantages of the invention are obtained by the drug delivery system comprising at least one core comprising therapeutically active substance(s), at least one membrane encasing the core and an intermediary layer of a substantially inert material applied between the core and the membrane or between two membrane layers. The intermediary layer is capable of preventing direct contact between the core and the membrane or between two membranes but is not covalently bound to either of them. Preferably said intermediary layer comprises particulate matter, particles, granules, crystals, micro- or nanoscaled crystals or powder in a solid, suspended or gel form.

According to an embodiment of the invention, the drug delivery system consists of one core comprising at least one therapeutically active substance, an intermediary layer applied on the surface of the core, and a membrane encasing the core and the intermediary layer.

According to another embodiment of the invention, the drug delivery system consists of at least two cores, at least one of the cores comprising a therapeutically active substance, an intermediary layer applied on the surface of at least the core(s) comprising the active substance, and a membrane encasing the cores and the intermediary layer(s).

According to a further embodiment of the invention, the drug delivery system consists of one core comprising at least one therapeutically active substance, a membrane encasing the core, an outer membrane encasing the core-membrane system and an intermediary layer applied between said membrane and outer membrane.

Any suitable design of the delivery system or any combination of structure is naturally possible and within the scope of the invention. Thus, the system can take a wide variety of shapes and forms for administering the therapeutically active agent at controlled rate to different areas of the body. The invention can be applied to any type of formulation as long as it comprises a core containing the therapeutically active agent, at least one membrane and an intermediary layer controlling the release of a therapeutically active agent. The delivery system may for example have a form of an implant, an intrauterine system (IUS), an intracervical device (ICD), a vaginal ring, a helical coil or a spring and a like.

According to the present invention the intermediary layer comprises a suitable inert material applied between the outer surface of the core and the inner surface of the membrane or when there are two or more membranes, between two membrane layers. The term "inert" or "substantially inert" means here a material which is not covalently bound to the core or membrane material and is not a polymer membrane. The intermediary layer prevents or at least decreases the direct contact between the core(s) and the membrane(s) and creates an additional diffusion layer with two interfaces forming between the core(s) and the membrane or between two membranes. The diffusion will not take place until the intermediary layer gets wet, for example when the external body fluid is absorbed through the membrane(s) in the target organ. For this reason the drug substance cannot migrate from the core to the membrane layer(s) during storage. This will eliminate or diminish initial burst and will further help to adjust the release rate of the therapeutically active substance.

Exemplary inert material or combination of materials comprising particulate matter, particles, granules, crystals, micro- or nanoscaled crystals or powder in a solid, suspended or gel form that can in practice be used as an intermediary layer in the drug delivery system according to the present invention include inorganic salts, e.g. calcium sulphate, magnesium sulphate, sodium carbonate, calcium carbonate and barium sulphate, organic salts such as sodium lactate and other organic compounds such as saccharides, e.g. mono- and polysaccharides such as starch, methyl cellulose, croscarmellose sodium, microcrystalline cellulose, hydroxypropylcellulose, hydroxypropylmethylcellulose, dextrin, lactose, sucrose, fructose, trehalose, sugar alcohols, polyols and crystalline sugars, mannitol, sorbitol, xylitol, carboxymethylcellulose and salts thereof, organic non saccharides, e.g. povidone, polymers, silica and high surface area fumed and precipitated silicas, talc, barytes, lithopone, metal oxides such as zinc oxide, iron oxide, aluminium oxide and titanium dioxide, clays such as kaolin, crushed quartz, diatomaceous earths, polyalkylene glycol and the like. Preferably the material is non-swellable or only slightly swellable in biological fluids. In the drug delivery system according to the present invention the substantially inert material is selected from the group consisting of silica, fumed and precipitated silica and talc.

The core of the delivery system consists essentially of a polymer composition, that is, the core is a polymer matrix wherein the therapeutically active substance or substances are dissolved or dispersed. The polymer composition of the core is permeable to the therapeutically active substance. Depending on the delivery system, the core(s) may be solid or hollow. Hollow cores can be easily assembled for example on the body of an intrauterine system. In addition, by using hollow cores a continuous cavity formed inside a vaginal ring reduces the overall weight of the device and influences beneficially the elasticity, flexibility and softness of the ring which all may give better wearing comfort for the user. The cores may also comprise a support member consisting of an inert material, for example a polymer rod or a metal wire, to modify the elasticity or flexibility of the core. The delivery system of the present invention can also be applied for example on the surface of a medical device, such as a stent or a catheter.

According to the embodiment in which the delivery system consists of two or more cores, said cores are preferably positioned next to each other. The length of the compartments may be same or different. The cores may or may not be separated from each other by a separation membrane or by an inert placebo core.

The membrane comprises a polymer composition which is permeable to the therapeutically active substance but preferably less permeable than the polymer composition of the core. Although the membrane may cover only a part of the delivery system, it advantageously encases the whole delivery system. The thickness of the membrane depends on materials and active agents used as well as on the desired release profiles, but generally the thickness is smaller than the thickness of the core member.

The membrane may consist of more than one layer, in which case each layer has a certain thickness, and the thickness of the layers may be the same or different. The combination of different membrane layers either in design, thickness or in material or both, gives a further possibility for controlling the release rates of the active agents.

Polymer compositions of the core, the membrane and the possible separation membrane or the inert placebo compartment, can be the same or different and may stand for one single polymer, a mixture of polymers or the polymer composition may be made up of polymers that are blended with each other.

In principle any polymer, either biodegradable or non-biodegradable, can be used as long as it is biocompatible. Polysiloxanes, in particular poly (dimethyl siloxane) (PDMS) and modified poly (dimethyl siloxanes), are highly suitable for use as a membrane or core material. Further examples of suitable materials include, but are not limited to, copolymers of dimethylsiloxanes and methylvinylsiloxanes, ethylene/vinyl acetate copolymers (EVA), polyethylene, polypropylene, ethylene/propylene copolymers, acrylic acid polymers, ethylene/ethyl acrylate copolymers, polytetrafluoroethylene (PTFE), polyurethanes, thermoplastic polyurethanes, polyurethane elastomers, polybutadiene, polyisoprene, poly(methacrylate), polymethyl methacrylate, styrene-butadiene-styrene block copolymers, styrene-isobutylene-styrene copolymers, poly(hydroxyethylmethacrylate) (pHEMA), polyvinyl chloride, polyvinyl acetate, polyethers, polyacrylonitriles, polyethylene glycols, polymethylpentene, polybutadiene, polyhydroxy alkanoates, poly(lactic acid), poly(glycolic acid), polyanhydrides, polyorthoesters, hydrophilic polymers such as the hydrophilic hydrogels, cross-linked polyvinyl alcohol, neoprene rubber, butyl rubber, hydroxyl-terminated organopolysiloxanes of the room temperature vulcanizing type which harden to elastomers at room temperature following the addition of cross-linking agents in the presence of curing catalysts, one- or two-component dimethylpolysiloxane compositions cured by hydrosilylation at room temperature or under elevated temperatures, as well as mixtures thereof.

The structural integrity of the material, especially that of the membrane, may be enhanced by the addition of filler such as silica or diatomaceous earth. The polymers can also be mixed with other additives, for example to adjust their hydrophilic or hydrophobic properties, while taking into account that all additives need to be biocompatible and harmless to the patient.

The core or membrane may also comprise additional material to further adjust the release rate of one or several of the therapeutic substances. Auxiliary substances, for example such as tensides, anti-foaming agents, solubilisers or absorption retarders, or a mixture of any two or more of such substances, can also be added in order to impart the desired physical properties to the body of the delivery system. Further, additives such as pigments, glossing agents, matting agents, colorants, mica or equal can be added to the body of the delivery system or the membrane or to both in order to provide the delivery system with a desired visual appearance.

The amount of the therapeutically active agent incorporated in the delivery system varies depending on the particular therapeutically active agent, intended use of the substance, expected release rate and the time for which the system is expected to provide therapy. Since a variety of devices with varying sizes can be formulated for administering dosages, there is no critical upper limit on the amount of therapeutically active agent incorporated in the device.

The lower limit depends on the activity of the therapeutically active agent and the expected release time. A person skilled in the art is readily able to determine the amount of the therapeutically active agent needed for each specific application of the delivery system.

Preferably, the amount of a therapeutically active agent in the delivery system varies between almost zero to 60 wt-%, when it is mixed into the polymer, the preferred amount being between 10-40 wt-% of the weight of the delivery system. Other possible ranges of the amount of the therapeutically active agent are 0.5-60 wt-%, 5-55 wt-%, 10-45 wt-%, 25-60 wt-%, 40-50 wt-% and 15-35 wt-%. Since the release rate is relatively constant during the whole time of usage, a lower amount of drug will be often sufficient to achieve necessary period of administration as compared to the traditional delivery systems, where the drug load is partly consumed by initial burst.

The daily dosage of the therapeutically active substances for a defined condition to be treated and for a defined substance can be achieved with the delivery system according to the invention particularly by varying the polymer composition of the core or membrane or both and by varying the material of the intermediary layer, the amount and/or the properties of the layer, for example thickness, size and crystal form of the particles etc. For optimal performance the particle size is below 300 microns, preferably from 5 to 250 microns or from 20 to 200 microns. In addition, other parameters such as the size and form of the device and the drug load will influence the daily dose released from said device. Some, but not undue, experimentation will be needed to find the most suitable parameters for each combination.

Depending on the type and the use of the device, the expected practical life-time of the device varies from one week to several years, for example from one year to 7 years, preferably from 1 year to 5 years, or from one week to 12 months, preferably from one week to 6 months and more preferably from 21 days to 3 months.

The drug delivery system according to this invention can be manufactured by any technique known in the art. The therapeutically active agent may be mixed within the core material, processed to the desired shape by moulding, injection moulding, rotation/injection moulding, casting, extrusion, such as co-extrusion, coating extrusion, sequential extrusion and/or blend-extrusion or other appropriate methods.

The intermediary layer can be produced by encasing, coating, dusting or smoothing the surface of the core or the membrane by the inert material. For example, granules, particles, crystals, microcrystals, powder or suspension of an inert material can be adhered on the sticky or gummy surface of the core, the core or a part of it can be sprayed with the material or with a suspension of said material in a suitable solvent, the core can be dipped in such a suspension, or the surface of the core can be wetted by a suitable liquid, for example a solvent or silicone oil and then the core is dipped in the inert material, finally by letting the solvent, if any, to evaporate. The inert solid material can be mixed or suspended in a carrier material known in the art, for example silicone oil or hard fat or other encapsulation material, which is then applied on the surface of the core.

The membrane layer can be applied on the core and on the intermediary layer according to known methods, for example by mechanical stretching or expanding a prefabricated, tube formed membrane by using pressurised gas like air or by swelling in a suitable solvent like cyclohexane, diglyme, propanol, isopropanol or a mixture of solvents, or preferably by extrusion, moulding, spraying or dipping. The ends of the drug delivery system can be combined by known methods to produce a vaginal delivery device. When the delivery system is intended to be in the form of rod or a medicated capsule, e.g. an implant or an intrauterine system, the ends of the core-membrane rod can be sealed during the extrusion process or by using an adhesive.

EXPERIMENTAL

The ability to control and fine tune the release rate and to control the initial burst effect was demonstrated with levonorgestrel containing implants. A core comprising an intermediary layer and a core comprising an intermediary layer and a membrane were made and the results were compared to a corresponding core with a membrane but without any intermediary layer. The samples have been manufactured by coating extrusion and the ends of the samples have been sealed.

The content of the therapeutically active agent in the core is 50 wt-% (weight percent), and the agent was mixed in the elastomer with a mixer before extrusion.

The diameter of the cores used in experiments is 2.0 mm and the length is 20 mm. The thickness of the membrane is 0.3 mm.

Figure 2:
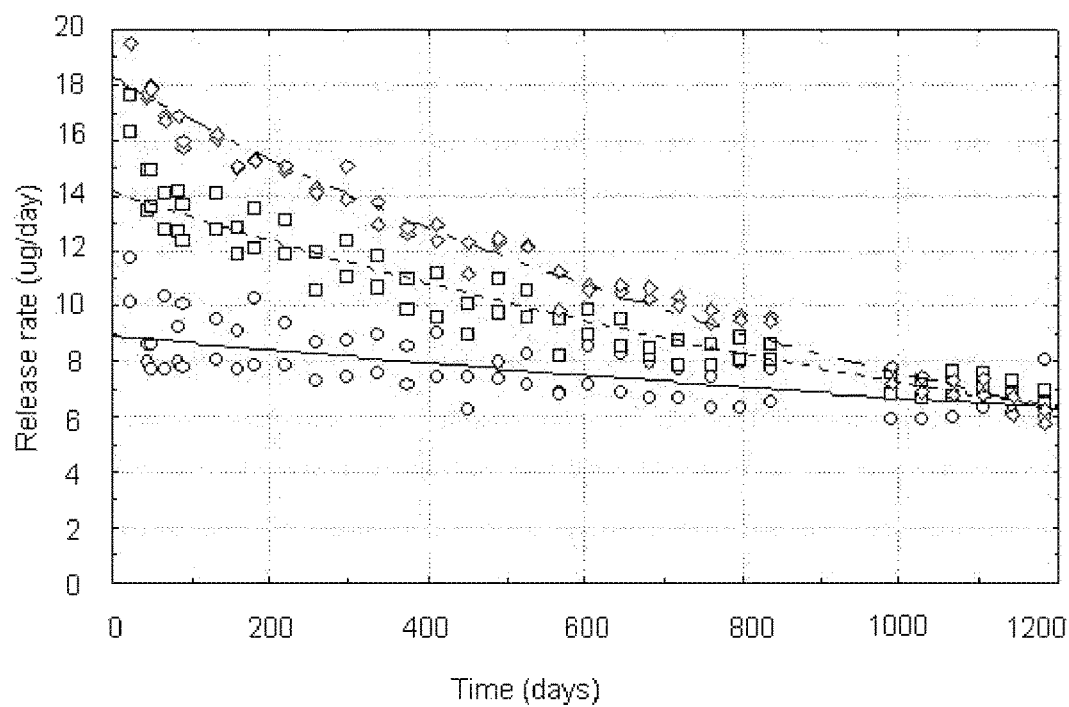
FIG. 2 illustrates an example of the release rates. First release profile has been derived for a prior art core encased by a membrane (losenges), the second release profile for a core the surface of which has been covered by silicon oil (squares) and the third release profile for a core covered by silica particles and then encased by a membrane (circles). The samples have been manufactured by coating extrusion and the ends of the samples have been sealed.
Figure 3:
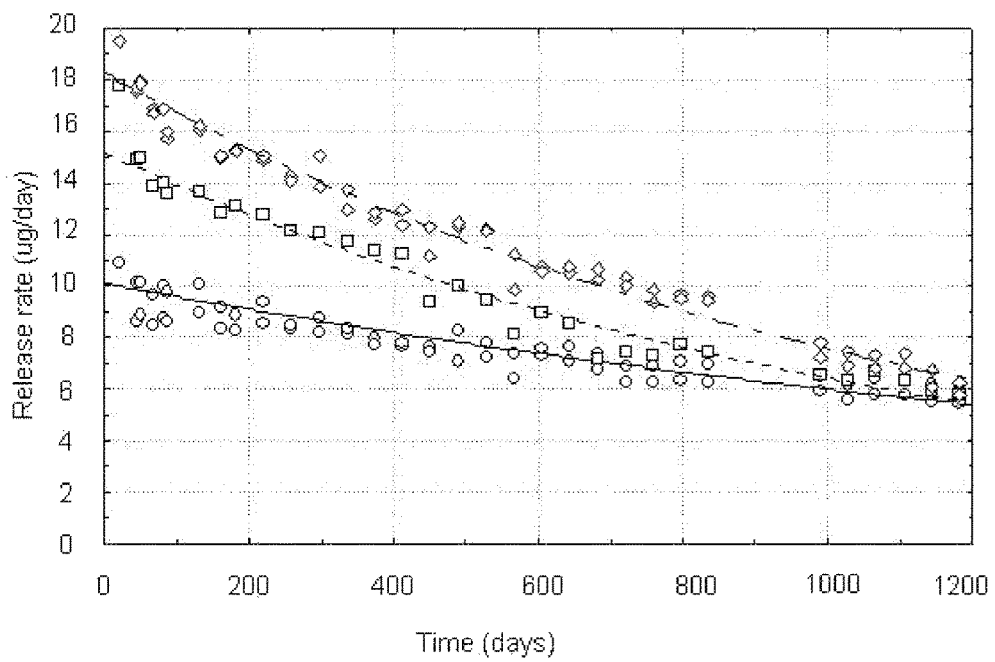
FIG. 3 illustrates another example of the release rates. First release profile has been derived for a prior art core encased by a membrane (losenges), the second release profile for a core the surface of which has been covered by silica particles (squares) and the third release profile for a core covered by silica particles and then encased by a membrane (cirdes). The samples have been manufactured by coating extrusion and the ends of the samples have been sealed.

The results are shown in FIGS. 2 and 3 for the daily in vitro release rate, shown as the y axis and days shown in the x-axis, wherein the losenges represent the results for a prior art core encased by a membrane, squares illustrate the results for a core the surface of which has been covered by silica particles, and the circles represent the results for a core covered by silica particles and encased by a membrane.

Figure 4:
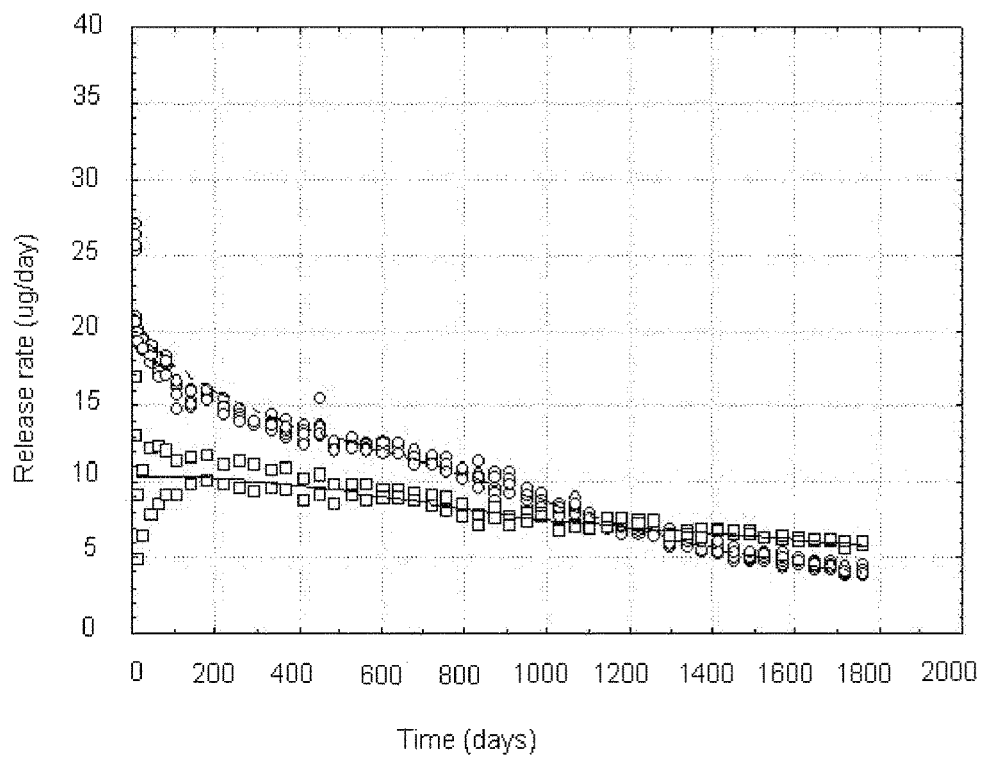
FIG. 4 illustrates a further example of the release rates. First release profile has been derived for a prior art core comprising levonorgestrel and encased by a membrane (cirdes), and the second release profile for a core comprising levonorgestrel, wherein the surface of the core has been coated by talcum particles and the whole system has been encased by a membrane (squares). The samples have been manufactured by coating extrusion and the ends of the samples have been sealed. The release profile has been calculated from the data of the accelerated release test of levonorgestrel at 60° C. and corresponds to the release rate of 5 years.

The present invention was also tested by using talcum as the intermediary layer. The results are shown in FIG. 4 for the daily in vitro release rate, shown as the y axis and days shown in the x-axis, wherein the losenges represent the results for a prior art core comprising levonorgestrel and encased by a membrane, and the squares represent the results for a core comprising levonorgestrel, the surface of which has been coated by talcum particles and the whole system has been encased by a membrane. The samples have been manufactured by coating extrusion and the ends of the samples have been sealed. The release profile has been calculated from the data of the accelerated release test of levonorgestrel at 60° C. and corresponds to the release rate of 5 years.

The results show that compared to the reference samples, the samples comprising the intermediary layer have lower initial dose and lower daily dose over a relatively long period of time, and the decrease is more enhanced with the samples comprising both an intermediary layer and a membrane encasing the core and said intermediary layer. Further, as can be seen in FIGS. 2-4 the samples comprising the intermediary layer and the membrane have surprisingly constant release rate of the active drug substance as compared to the reference samples.

The invention is described below in greater detail in the following, non-limiting examples.

Example 1

Core Preparation 50 parts by weight of levonorgestrel and 50 parts by weight of poly (dimethylsiloxane-covinylmethylsiloxane) and 1.2 parts by weight of dichlorobenzoylperoxide-polydimethylsiloxane paste (50% of dichlorobenzoylperoxide) were mixed with a 2-roll mill. The mixture was extruded to a rod-like form having the outer diameter of 2.0 mm and cured by heat at +150° C. for 15 minutes, during which crosslinking took place. The resulting rod was cut into cores having the length of 20 mm.

Part of the cores were treated with a thin layer of silicon oil and covered by a layer of silica particles, while another part of the cores were covered by a talcum layer. The reference cores remained intact, without any coating.

Membrane Preparation 9 parts of PEO-b-PDMS, 89 parts of silica-filled poly (dimethylsiloxane-covinylmethylsiloxane), 10 ppm Pt-catalyst (of the reaction species), 0.03 parts inhibitor (ethynyl cyclohexanol), and approximately 2 parts of poly-(hydrogenmethylsiloxane-codimethylsiloxane) crosslinker were mixed in a two-roll mill. The membrane material was coating extruded on the above prepared cores, i.e. half of the cores coated with silica layer, talcum layer and cores without any intermediary layer, by successively inserting them through the inner nozzle in the die. The wall thickness of the resulting membrane was 0.3 mm.

Example 2. Preparation of the Intrauterine Delivery System 50 parts by weight of levonorgestrel and 50 parts by weight of poly (dimethylsiloxane-covinylmethylsiloxane) and 1.2 parts by weight of dichlorobenzoylperoxide-polydimethylsiloxane paste (50% of dichlorobenzoylperoxide) were mixed with a 2-roll mill. The mixture was extruded to a tube-like form having the outer diameter of 2.0 mm and the wall thickness of 0.5 mm. The extrudate was cured by heat at +150° C. for 15 minutes, during which crosslinking took place. The resulting tube was cut into cores having the length of 20 mm.

The core was treated with a thin layer of silicon oil and covered by a talcum layer. The membrane material prepared according to example 1 was coating extruded on the core. The wall thickness of the resulting membrane was 0.3 mm.

The tube-like reservoir was swollen in cyclohexane and assembled on the vertical stem of a T-shaped IUS body. Cyclohexane was allowed to evaporate. The ends of the reservoir were sealed by using silicone glue.

Example 3. Preparation of a Vaginal Delivery System 50 parts by weight of levonorgestrel, 50 parts by weight of poly (dimethylsiloxane-covinylmethylsiloxane) and 1.2 parts by weight of dichlorobenzoylperoxide-polydimethylsiloxane paste (50% of dichlorobenzoylperoxide) were mixed with a 2-roll mill. The mixture was extruded to a core having the outer diameter of 2.8 mm and cured by heat at +150° C. for 15 minutes, during which crosslinking took place. The crosslinked core was cut into 167 mm length.

99 parts of silica-filled poly (dimethylsiloxane-co-vinylmethylsiloxane), 10 ppm Ptcatalyst (of the reaction species) and 0.03 parts of inhibitor (ethynyl cyclohexanol) and approximately 0.6 parts of poly (hydrogenmethylsiloxane-co-dimethylsiloxane) cross linker were mixed in a 2-roll mill. The membrane material was coating extruded on the core prepared above. The wall thickness of the resulting membrane was 0.23 mm.

The ends of the membrane coated core are joined together into a closed system either by using a biocompatible adhesive or preferably by using a 10 mm long polyethylene rod having outer diameter of 1.2 mm as a coupling means. An adhesive (Nusil Med 1-4213) is spread on the other end of the coupling means and polyethylene rod is pushed approximately 5 mm into the core. The cross sectional surfaces of the core-membrane tube and the other end of the coupling means are dabbed with the same adhesive and the other end of the core-membrane system is pushed over the polyethylene rod so that the ends of the core-membrane system meet each other. The adhesive is cured at 100° C. for 1 hour.

Drug Release Test

The release rate of the drug from the implant was measured in vitro as follows:

The intrauterine delivery systems were attached into a stainless steel holder in vertical position and the holders with the devices were placed into glass bottles containing 250 ml of a dissolution medium. The glass bottles were shaken in shaking water bath 100 rpm at 37° C. The dissolution medium was withdrawn and replaced by a fresh dissolution medium at predetermined time intervals, and the amount of the released drug was analysed by using standard HPLC methods. The concentration of the dissolution medium and the moment of change (withdrawal and replacement) of medium were selected so that sink-conditions were maintained during the test.

Although the invention has been described in terms of particular embodiments and applications, one of ordinary skill in the art can in light of this teaching generate additional embodiments and modifications without departing from the spirit of or exceeding the scope of the claimed invention. Accordingly, it is to be understood that the drawings and descriptions herein are offered by way of example to facilitate comprehension of the invention and should not be construed to limit the scope thereof.

The invention claimed is:

1. A drug delivery system comprising at least one core comprising Levonorgestrel and at least one membrane encasing the core, wherein the system further comprises an intermediary layer consisting of a substantially inert material and optionally a liquid solvent or silicone oil, wherein the intermediary layer is not covalently bound to the material of the core and is not covalently bound to the material of the at least one membrane and the substantially inert material is selected from the group consisting of silica, and fumed and precipitated silicas to maintain at least substantially constant release of the Levonorgestrel during course of usage with no or diminished initial burst as compared to a delivery system without the intermediary layer, wherein the drug delivery system has a release rate that is relatively constant for from 1 week to 7 years.

2. A drug delivery system according to claim 1, characterized in that the substantially inert material is in a form which is at least one selected from the group consisting of particulate matter, particle, granule, crystal, microscaled crystal, nanoscaled crystal, powder in a solid form, suspended powder, and powder in a gel form.

3. A drug delivery system according to claim 1, characterized in that the intermediary layer of a substantially inert material is applied between the core and the membrane.

4. A drug delivery system according to claim 1, characterized in that the intermediary layer of a substantially inert material is applied between two membrane layers.

5. A drug delivery system according to claim 1, characterized in that the system is a vaginal delivery system, an implant, an intrauterine delivery system, an intracervical delivery system, a helical coil or a spring, wherein the core is at least 20 mm in length.

6. A drug delivery system according to claim 1, further including a coating of an adherent over the core and wherein the substantially inert material covers the coating.

7. A drug delivery system according to claim 6, wherein the adherent is silicone oil.

8. A drug delivery system according to claim 1 wherein the drug delivery system has a release rate that is relatively constant for 21 days.

9. A drug delivery system according to claim 1 wherein the drug delivery system has a release rate that is relatively constant for 3 months.

10. The drug delivery system according to claim 1, wherein the drug delivery system is an intrauterine system;
   wherein the core is a polymer matrix comprising a first polymer where the one or more therapeutically active substance(s) are dissolved or dispersed;
   wherein the at least one membrane encasing the core comprises a second polymer; and
   wherein the first polymer and the second polymer are each a polysiloxane.

11. A drug delivery system according to claim 1, wherein the drug delivery system has a release rate that is relatively constant from 1 week to 12 months.

12. A drug delivery system according to claim 1, wherein the drug delivery system has a release rate that is relatively constant from 1 year to 5 years.

* * * * *